United States Patent
Choi et al.

(10) Patent No.: US 10,207,966 B2
(45) Date of Patent: Feb. 19, 2019

(54) PROCESS FOR ENHANCING THE PERFORMANCE OF THE DEHYDROGENATION OF ALKANES

(71) Applicant: SABIC GLOBAL TECHNOLOGIES B.V., Bergen op Zoom (NL)

(72) Inventors: YongMan Choi, Riyadh (SA); Ramsey Bunama, Riyadh (SA); Khalid M. El-Yahyaoui, Riyadh (SA)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 15/540,136

(22) PCT Filed: Dec. 29, 2015

(86) PCT No.: PCT/IB2015/060028
§ 371 (c)(1),
(2) Date: Jun. 27, 2017

(87) PCT Pub. No.: WO2016/108184
PCT Pub. Date: Jul. 7, 2016

(65) Prior Publication Data
US 2017/0369399 A1    Dec. 28, 2017

Related U.S. Application Data

(60) Provisional application No. 62/098,782, filed on Dec. 31, 2014.

(51) Int. Cl.
*C07C 5/333* (2006.01)
*C07C 5/32* (2006.01)
(Continued)

(52) U.S. Cl.
CPC ............ *C07C 5/3332* (2013.01); *C07C 11/02* (2013.01); *C07C 11/09* (2013.01);
(Continued)

(58) Field of Classification Search
CPC ....... C07C 5/333; C07C 5/3332; C07C 11/09; C07C 11/02
See application file for complete search history.

(56) References Cited

U.S. PATENT DOCUMENTS

| 5,133,947 A | 7/1992 | Stambaugh et al. |
| 5,641,842 A | 6/1997 | McDaniel et al. |

FOREIGN PATENT DOCUMENTS

| CN | 101268912 A | 7/2009 |
| CN | 101468889 A | 7/2009 |

(Continued)

OTHER PUBLICATIONS

Ding et al. (Coupling dehydrogenation of isobutane in the presence of carbon dioxide over chromium oxide supported on active carbon, 2008, 19, 1059-1062) (Year: 2008).*

(Continued)

*Primary Examiner* — Youngsul Jeong
(74) *Attorney, Agent, or Firm* — Cantor Colburn LLP

(57) ABSTRACT

A process of catalytically dehydrogenating an alkane to an alkene, using $Cr_2O_3$ as a catalyst, where the catalyst is oxidized to $CrO_3$ during the dehydrogenation, and is regenerated by using CO as a reducing gas. In regenerating the catalyst with CO, $CO_2$ is produced, which may be fed to a dehydrogenation reactor with the alkane and reacted with $H_2$ produced by the dehydrogenation, to form CO and $H_2O$ by the reverse water-gas shift reaction.

11 Claims, 1 Drawing Sheet

(51) Int. Cl.
*C07C 11/02* (2006.01)
*C07C 11/09* (2006.01)

(52) U.S. Cl.
CPC ...... *C07C 2521/04* (2013.01); *C07C 2521/06* (2013.01); *C07C 2523/26* (2013.01); *Y02P 20/146* (2015.11); *Y02P 20/584* (2015.11)

(56) References Cited

FOREIGN PATENT DOCUMENTS

| CN | 101468910 A | 7/2009 |
|----|-------------|--------|
| CN | 101468911 A | 7/2009 |
| CN | 101468912 A | 7/2009 |
| CN | 101234238 B | 12/2010 |
| CN | 103242058 A | 8/2013 |

OTHER PUBLICATIONS

Airaksinen et al. (Effect of catalyst prereduction on the dehydrogenation of isobutane over chromia/alumina, Ind. Eng. Chem. Res. 2005, 44, 3862-3868) (Year: 2005).*

Airaksinen et al., "Effect of Catalyst Prereduction on the Dehydrogenation of Isobutane over Chromia/Alumina," Ind. Eng. Chem. Res. 2005, vol. 44, pp. 3862-3868.

Cavani et al. "Chemical and Physical Characterization of Alumina-Suppored Chromia-Based Catalysts and Their Activity in Dehydrogenation of Isobutane", Journal of Catalysis, 1996, vol. 158, pp. 236-250.

Chinese Patent No. 101234238; Date of Publication: Aug. 6, 2008; Abstract Only, 1 page.

Chinese Patent No. 101468889; Date of Publication: Jul. 1, 2009; Abstract Only, 1 page.

Chinese Patent No. 101468910; Date of Publication: Jul. 1, 2009; Abstract Only, 1 page.

Chinese Patent No. 101468911; Date of Publication: Jul. 1, 2009; Abstract Only, 1 page.

Chinese Patent No. 101468912; Date of Publication: Jul. 1, 2009; Abstract Only, 1 page.

Chinese Patent No. 103242058; Date of Publication: Aug. 14, 2013; Abstract Only, 1 page.

Ding et al., "Coupling dehydrogenation of isobutane in the presence of carbon dioxide over chromium oxide supported on active carbon," Chinese Chemical Letters 19 (2008) pp. 1025-1062.

International Search Report for International Application No. PCT/IB2015/060028; International Filing Date: Dec. 29, 2015; dated Mar. 11, 2016; 5 Pages.

Neugebauer et al. "The Heat of Formation of Ammonium Dichromate", The Journal of Physical Chemistry, 1957, vol. 61, pp. 1429-1430.

Written Opinion of the International Searching Authority for International Application No. PCT/IB2015/060028; International Filing Date: Dec. 29, 2015; dated Mar. 11, 2016; 6 Pages.

* cited by examiner

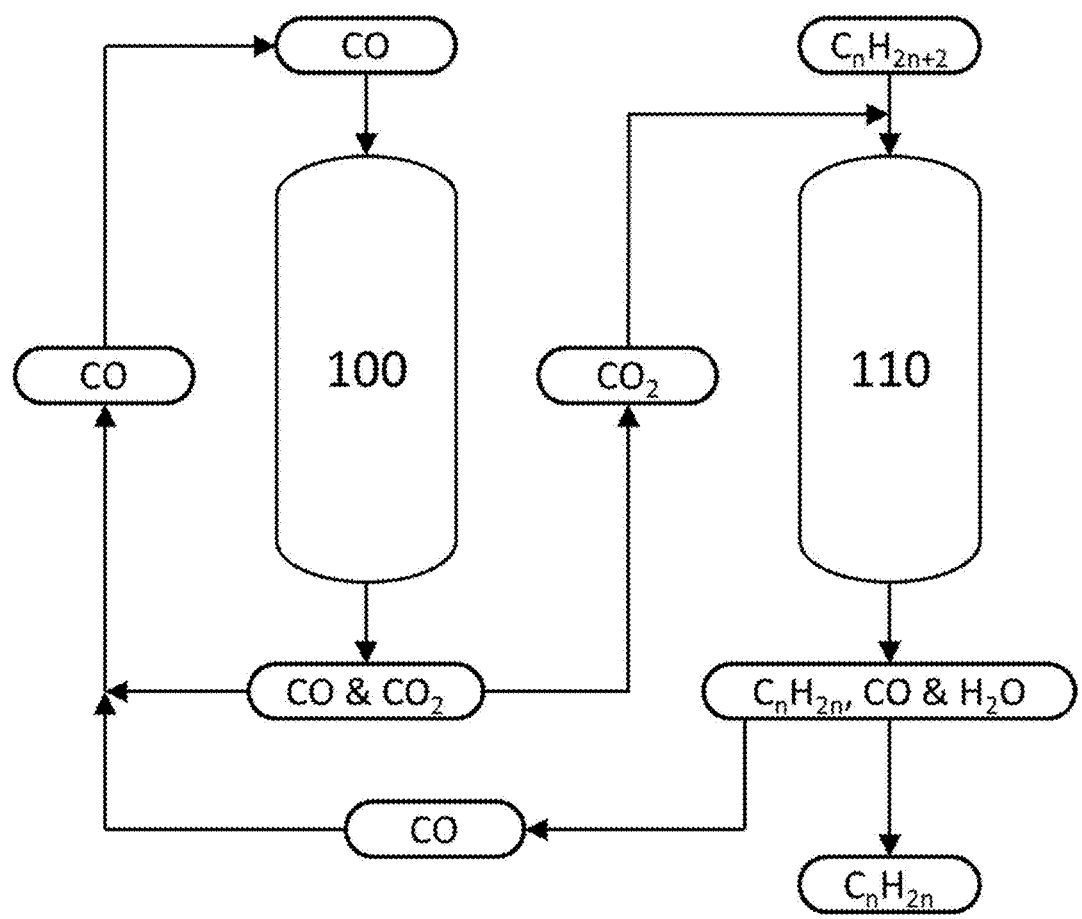

PROCESS FOR ENHANCING THE PERFORMANCE OF THE DEHYDROGENATION OF ALKANES

CROSS REFERENCE TO RELATED APPLICATIONS

This application is a 371 of International Application No. PCT/IB2015/060028, filed Dec. 29, 2015, which claims priority to U.S. Application Ser. No. 62/098,782, filed Dec. 31, 2014 which are incorporated herein by reference in their entirety.

BACKGROUND

Field of the Invention

The present invention relates to processes for dehydrogenating alkanes to alkenes, specifically alkane dehydrogenation processes using a chromium oxide catalyst, a method for decreasing the temperature and/or increasing the efficiency of an alkane dehydrogenation process, and a composition formed by dehydrogenating an alkane with a chromium oxide catalyst.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Alkenes are one of the most important feedstocks for industrial chemical purposes, since they can participate in a wide variety of reactions. For example, ethylene and propylene can be polymerized to form polyethylene and polypropylene, respectively, and isobutylene can be reacted with methanol to form methyl tert-butyl ether (MTBE). Alkenes, however, are far less naturally abundant than their alkane counterparts.

Alkanes are obtained in abundant quantities as byproducts of fossil fuel refining processes, and are useful precursors for the more industrially relevant alkenes. For example, alkenes are produced from alkanes industrially by thermal cracking and steam cracking. Alkanes also may be catalytically dehydrogenated to alkenes by the following endothermic reaction:

$$C_nH_{2n+2} \rightarrow C_nH_{2n} + H_2 \quad \Delta H_R° > 0 \quad (R1)$$

Hydrogen-containing gases, such as $H_2$ and $CH_4$, are typically used in a reduction cycle to reduce the catalyst, for example reducing the chromium from an oxidation state of $Cr^{6+}$ to $Cr^{3+}$ in a chromium oxide catalyst.

Because alkane dehydrogenation reactions are highly endothermic, they require high temperatures to obtain acceptable yields. However, these high temperatures enhance undesired side reactions, including the formation of carbonaceous coke deposits on the catalyst bed. Coke buildup adversely affects catalyst performance, leading to lower yields and expensive maintenance. For example, once catalysts have been deactivated by coke buildup, they must be taken offline and regenerated, typically by burning off the coke deposits with oxygen. Time spent offline reduces overall reactor efficiency.

SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawing.

One aspect of the present invention includes a process of dehydrogenating an alkane to an alkene, including:
(a) feeding CO to a reactor containing a catalyst comprising $CrO_3$;
(b) contacting the CO with the $CrO_3$, to form $Cr_2O_3$ and $CO_2$;
(c) feeding an alkane to the reactor; and
(d) contacting the alkane with the catalyst to form an alkene and $H_2$.

A second aspect of the present invention includes a process of dehydrogenating an alkane to an alkene, including:
(a) feeding CO to a first reactor containing a catalyst comprising $CrO_3$;
(b) contacting the CO with the $CrO_3$, to form $Cr_2O_3$ and $CO_2$;
(c) feeding the $CO_2$ obtained in (b), and an alkane, to a second reactor containing a catalyst comprising $Cr_2O_3$;
(d) contacting the alkane with the catalyst in the second reactor to form an alkene and $H_2$;
(e) reacting the $CO_2$ from (c) with the $H_2$ from (d), in the second reactor, to form CO and $H_2O$; and
(f) feeding the CO formed in (e) to (a).

A third aspect of the present invention includes a process of dehydrogenating an alkane to an alkene, including:
performing (a)-(f) for a time X
(a) feeding CO to a first reactor containing a catalyst comprising $CrO_3$;
(b) contacting the CO with the $CrO_3$, to form $Cr_2O_3$ and $CO_2$;
(c) feeding the $CO_2$ obtained in (b), and an alkane, to a second reactor containing a catalyst comprising $Cr_2O_3$;
(d) contacting the alkane with the catalyst in the second reactor to form an alkene and $H_2$;
(e) reacting the $CO_2$ from (c) with the $H_2$ from (d), in the second reactor, to form CO and $H_2O$; and
(f) feeding the CO formed in (e) to (a);
then performing (a')-(f') for a time X'
(a') feeding CO to the second reactor containing a catalyst comprising $CrO_3$;
(b') contacting the CO with the $CrO_3$, to form $Cr_2O_3$ and $CO_2$;
(c') feeding the $CO_2$ obtained in (b'), and an alkane, to the first reactor containing a catalyst comprising $Cr_2O_3$;
(d') contacting the alkane with the catalyst in the first reactor to form an alkene and $H_2$;
(e') reacting the $CO_2$ from (c') with the $H_2$ from (d'), in the first reactor, to form CO and $H_2O$; and
(f') feeding the CO formed in (e') to (a');
wherein (a)-(f) for the time X and (a')-(f') for the time X' are switched cyclically.

In another aspect of the process of dehydrogenating an alkane to an alkene, the alkane is a $C_2$-$C_{10}$ alkane.

In another aspect of the process of dehydrogenating an alkane to an alkene, the alkane is a $C_3$-$C_5$ alkane.

In another aspect of the process of dehydrogenating an alkane to an alkene, the alkane is isobutane.

In another aspect of the process of dehydrogenating an alkane to an alkene, the catalyst comprising $CrO_3$ and the catalyst comprising $Cr_2O_3$ comprise an alumina or zirconia support.

A fourth aspect of the present invention includes a method of improving catalyst efficiency and/or reducing catalyst fouling by recycling a regeneration feedstock.

A fifth aspect of the invention includes an alkene-containing composition obtained by dehydrogenating an alkane in the presence of a chromium oxide catalyst.

A sixth aspect of the invention includes a chromium oxide-containing catalyst obtained by reducing a catalyst with CO.

BRIEF DESCRIPTION OF THE DRAWING

A more complete appreciation of the disclosure and many of the attendant advantages thereof will be readily obtained as the same becomes better understood by reference to the following detailed description when considered in connection with the accompanying drawing, wherein:

The FIGURE shows a schematic diagram of an embodiment of the alkane dehydrogenation process disclosed herein.

DETAILED DESCRIPTION OF THE INVENTION

Conventional processes for catalytically dehydrogenating an alkane to an alkene use hydrogen-containing gases, such as $H_2$ and $CH_4$, in a reduction cycle to reduce the catalyst. Aspects of the present invention instead use CO as a reducing gas to reduce the catalyst. As shown below, a thermochemical analysis reveals that using CO as a reducing gas can provide more heat to the reactor bed than using $H_2$. This additional heat can aid in the endothermic dehydrogenation reaction of an alkane to an alkene.

In the thermochemical analysis, crystalline $CrO_3$ was used for simplicity. The enthalpy change for the reduction of $CrO_3$ with $H_2$ was calculated based on standard enthalpies of formation:

$$CrO_3(s) + 3/2 H_2(g) \rightarrow 1/2 Cr_2O_3(s) + 3/2 H_2O(g) \quad \Delta H_R^\circ = -336 \text{ kJ/mol} \quad (R2)$$

The enthalpy change for the reduction of $CrO_3$ with CO similarly was calculated based on standard enthalpies of formation:

$$CrO_3(s) + 3/2 CO(g) \rightarrow 1/2 Cr_2O_3(s) + 3/2 CO_2(g) \quad \Delta H_R^\circ = -397 \text{ kJ/mol} \quad (R3)$$

As seen from these calculations, both reduction reactions are highly exothermic. However, based on the calculations, reducing $CrO_3$ with CO provides an approximately 18% greater enthalpy change compared to reducing $CrO_3$ with $H_2$.

Because of the greater enthalpy change in reducing $CrO_3$ with CO compared to reducing $CrO_3$ with $H_2$, CO may be advantageously used to reduce a chromium oxide catalyst used in an endothermic alkane dehydrogenation reaction. The additional heat produced by reducing $CrO_3$ with CO and retaining the heat in a reactor means less energy needs to be supplied when performing a subsequent alkane dehydrogenation in the reactor. Additional heat in an amount of from 2 to 20%, preferably 4 to 18%, 6 to 16%, 8 to 14%, or 10 to 12%, based on the total enthalpy of the reduction of $CrO_3$ to $Cr_2O_3$ with CO, in comparison with the reduction of $CrO_3$ with $H_2$, can be obtained. The use of CO as a reducing gas to reduce a $CrO_3$ catalyst provides other benefits in addition to the enthalpic benefit described above. When an alkane is dehydrogenated to its corresponding alkene, other undesired alkanes and alkenes, as well as coke, may be produced as decomposition byproducts. For example, the dehydrogenation of isobutane ($i$-$C_4H_{10}$) to form isobutene ($i$-$C_4H_8$) may also produce decomposition byproducts including propane ($C_3H_8$), propylene ($C_3H_6$), ethane ($C_2H_6$), ethylene ($C_2H_4$) and methane ($CH_4$) by the following reactions:

$$i\text{-}C_4H_{10} \rightarrow i\text{-}C_4H_8 + H_2 \quad (R4)$$

$$i\text{-}C_4H_{10} + H_2 \rightarrow C_3H_8 + CH_4 \quad (R5)$$

$$C_3H_8 \rightarrow C_3H_6 + H_2 \quad (R6)$$

$$2CH_4 \rightarrow C_2H_6 + H_2 \quad (R7)$$

$$C_3H_8 \rightarrow C_2H_4 + CH_4 \quad (R8)$$

$$C_2H_6 \rightarrow C_2H_4 + H_2 \quad (R9)$$

The production of these decomposition byproducts requires the presence of hydrogen (see, e.g., reaction (R5)). Accordingly, it is advantageous to provide an alternate reaction pathway for hydrogen, so that decomposition reactions such as (R5) to (R9), as well as coke formation, are suppressed or eliminated. In aspects of the invention, the yield of any of $CH_4$, $C_3H_6$, $C_3H_8$, $C_2H_6$, or $C_2H_4$ during the dehydrogenation of isobutane ($i$-$C_4H_{10}$) to form isobutene, is less than 0.1 mass %, preferably less than 0.05 mass %, 0.001 mass %, 0.0005 mass %, 0.0001 mass %, 0.00005 mass % or less than 0.00001 mass % based on the total weight of the isobutane subjected to the dehydrogenation reaction.

As described above, reducing $CrO_3$ with CO results in the production of $CO_2$, as shown in reaction (R3). This $CO_2$ may be used as a scavenger to react with hydrogen produced in the subsequent alkane dehydrogenation reaction, thereby decreasing the amount of hydrogen available for facilitating decomposition reactions such as (R5) to (R9), and decreasing coke formation. The reaction of $CO_2$ with $H_2$ proceeds via the reverse water-gas shift reaction, as follows:

$$CO_2(g) + H_2(g) \rightarrow CO(g) + H_2O(g) \quad \Delta H_R^\circ = +41 \text{ kJ/mol} \quad (R10)$$

Decreasing the amount of hydrogen available in the dehydrogenation reactor in this way provides the additional benefit of shifting the equilibrium of the dehydrogenation reaction (R1) toward the product side, further improving reactor performance. Additionally, the CO produced in the reverse water-gas shift reaction can be recycled to regenerate the chromium oxide catalyst, according to reaction (R3).

The alkane dehydrogenation process may be performed continuously or in a batch operation. In a batch operation, the process may begin with a fresh catalyst comprising $Cr_2O_3$. After the dehydrogenation reaction is stopped, the $CrO_3$ may be contacted with CO to form $Cr_2O_3$, and the process may be repeated. Alternatively, the batch process may begin with partially or fully spent catalyst comprising $CrO_3$, which is initially contacted with CO to form $Cr_2O_3$ prior to performing the alkane dehydrogenation reaction, and the process may be repeated. In an exemplary embodiment more than 90% by mass, preferably more than 95% or 99% by mass of the chromium in the fresh catalyst is in the form of $Cr_2O_3$. Subsequent use in a dehydrogenation process may lower the amount of Cr present as $Cr_2O_3$ in the catalyst to form a spent catalyst in which from 40% by mass or less, preferably from 50% mass or less, 60% mass or less, 70% mass or less, 80% mass or less or 90% by mass or less, of the chromium is in the form of $Cr_2O_3$. Subsequent regeneration of the spent catalyst with CO forms a catalyst in which more than 90% by mass, preferably more than 95% or 99% by mass of the chromium is in the form of $Cr_2O_3$.

A non-limiting embodiment of a continuous process according to the second aspect is shown in the FIGURE. This process includes two reactors: a first reactor 100 containing a catalyst comprising $CrO_3$, and a second reactor 110 containing a catalyst comprising $Cr_2O_3$. Carbon monoxide is fed to the first reactor 100, and is contacted with the $CrO_3$ to form $Cr_2O_3$ and $CO_2$. Any excess, unreacted CO exits the first reactor 100, along with $CO_2$ produced according to reaction (R3) above. The CO and $CO_2$ are separated, and the CO may be recycled to the feed for the first reactor 100. The $CO_2$ produced in the first reactor 100 is fed to the second reactor 110, along with an alkane.

The alkane is dehydrogenated in the second reactor 110 by contacting it with a $Cr_2O_3$ catalyst to form an alkene and $H_2$ according to reaction (R1) above. The $CO_2$ produced in the first reactor 100 and fed to the second reactor 110 reacts with some or all of the $H_2$ in the second reactor 110 to form CO and $H_2O$, via the reverse water-gas shift reaction (R4) above. Additional $CO_2$, that is, $CO_2$ not produced in the first reactor 100, may also be supplied to the second reactor 110. The alkene, CO and $H_2O$ produced in the second reactor 110 exit the reactor and are separated. The CO from the second reactor 110 may be recycled to the feed for the first reactor 100.

The process depicted in the FIGURE may be performed for a specified time, for example until the performance of the $Cr_2O_3$ catalyst in the second reactor 110 has decreased beyond an acceptable level. After this time, the operation of the first reactor 100 and the second reactor 110 may be switched relative to each other, according to the third aspect. That is, after this time, the second reactor 110 contains a catalyst comprising $CrO_3$, and the first reactor 100 contains a catalyst comprising $Cr_2O_3$. Thus, CO is fed to the second reactor 110, and is contacted with the $CrO_3$ to form $Cr_2O_3$ and $CO_2$. Any excess, unreacted CO exits the second reactor 110, along with $CO_2$ produced according to reaction (R3) above. The CO and $CO_2$ are separated, and the CO may be recycled to the feed for the second reactor 110. The $CO_2$ produced in the second reactor 110 is fed to the first reactor 100, along with an alkane.

The alkane is dehydrogenated in the first reactor 100 by contacting it with the $Cr_2O_3$, to form an alkene and $H_2$ according to reaction (R1) above. The $CO_2$ produced in the second reactor 110 and fed to the first reactor 100 reacts with some or all of the $H_2$ in the first reactor 100 to form CO and $H_2O$, via the reverse water-gas shift reaction (R4) above. Additional $CO_2$, that is, $CO_2$ not produced in the second reactor 110, may also be supplied to the first reactor 100. The alkene, CO and $H_2O$ produced in the first reactor 100 exit the reactor and are separated. The CO from the first reactor 100 may be recycled to the feed for the second reactor 110.

This process, in which the operation of the first reactor 100 and the second reactor 110 are switched relative to their initial operation, may be performed for a specified time, for example until the performance of the $Cr_2O_3$ catalyst in the first reactor 100 has decreased beyond an acceptable level. After this time, the operation of the first reactor 100 and the second reactor 110 may be switched again relative to each other, back to their initial configuration. This cyclic operation of the first reactor 100 and the second reactor 110 may continue indefinitely, with periodic switching between one reactor performing catalytic dehydrogenation and the other reactor undergoing catalyst regeneration.

Although the FIGURE depicts a single reactor performing catalytic dehydrogenation and a single reactor undergoing catalyst regeneration, another aspect includes multiple reactors of each configuration at any one time. That is, one or more reactors may perform the catalytic dehydrogenation while one or more reactors undergo catalyst regeneration.

The amount of CO fed to the reactor containing a catalyst comprising $CrO_3$ may vary depending on the amount of the catalyst in the reactor, and the extent of conversion from $Cr_2O_3$ to $CrO_3$ in the catalyst. Preferably, CO is fed to the reactor at a space velocity of 0.100 l/s or more, 0.110 l/s or more, 0.120 l/s or more, 0.130 l/s or more, or about 0.137 l/s, and 0.170 l/s or less, 0.160 l/s or less, 0.150 l/s or less, or 0.140 l/s or less, based on the catalyst bed volume. Preferably, CO is fed to the reactor at a gas volumetric flow rate of 20.0 $m^3/s$ or more, 21.0 $m^3/s$ or more, 22.0 $m^3/s$ or more, 23.0 $m^3/s$ or more, 24.0 $m^3/s$ or more, or about 24.7 $m^3/s$, and 29.0 $m^3/s$ or less, 28.0 $m^3/s$ or less, 27.0 $m^3/s$ or less, 26.0 $m^3/s$ or less, or 25.0 $m^3/s$ or less, based on the mass of the catalyst.

The amount of $CO_2$ produced in the reactor by reducing the $CrO_3$ with CO may vary depending on the amount of the catalyst in the reactor, and the flow rate of CO into the reactor. Additional $CO_2$ may be supplied to the reactor performing the alkane dehydrogenation, to augment the $CO_2$ produced by reducing the $CrO_3$ with CO. The amount of additional $CO_2$ is preferably from 0.1 to 100 times the amount of $CO_2$ produced by reducing the $CrO_3$ with CO, more preferably from 1 to 50 times, or 5 to 10 times.

The temperature in the reactor during the reduction of $CrO_3$ with CO may vary depending on the flow rate of CO into the reactor. Preferably, the temperature in the reactor during the reduction of $CrO_3$ with CO is 550 to 600° C., or about 580° C., and the pressure in the reactor is 0.8 to 1.2 atm, or about 1 atm.

The alkane fed to the reactor performing the alkane dehydrogenation may be derived from a fossil fuel refining process, and may be supplied from a liquefied petroleum gas source. The alkane is preferably fed to the reactor in a gas or vapor phase. The alkane may be a straight-chain alkane or a branched alkane. It is preferably a $C_2$-$C_{10}$ alkane, more preferably a $C_3$-$C_5$ alkane, more preferably isobutane. The alkene produced in the dehydrogenation reaction is preferably a $C_2$-$C_{10}$ alkene, more preferably a $C_3$-$C_5$ alkene, more preferably isobutene.

The amount of the alkane fed to the reactor performing the alkane dehydrogenation may vary depending on the amount of the catalyst in the reactor, the amount of $CO_2$ fed to the reactor with the alkane, and the temperature in the reactor. Preferably, the alkane is fed to the reactor at a space velocity of 0.100 l/s or more, 0.110 l/s or more, 0.120 l/s or more, 0.130 l/s or more, or about 0.137 l/s, and 0.170 l/s or less, 0.160 l/s or less, 0.150 l/s or less, or 0.140 l/s or less, based on the catalyst bed volume. Preferably, the alkane is fed to the reactor at a gas volumetric flow rate of 20.0 $m^3/s$ or more, 21.0 $m^3/s$ or more, 22.0 $m^3/s$ or more, 23.0 $m^3/s$ or more, 24.0 $m^3/s$ or more, or about 24.7 $m^3/s$, and 29.0 $m^3/s$ or less, 28.0 $m^3/s$ or less, 27.0 $m^3/s$ or less, 26.0 $m^3/s$ or less, or 25.0 $m^3/s$ or less, based on the mass of the catalyst.

The catalyst comprising $Cr_2O_3$ used for the alkane dehydrogenation preferably comprises a support component in addition to the chromium component. The support component may comprise silica, alumina, boria, magnesia, thoria, titania, zirconia, or mixtures of two or more thereof. The support component preferably comprises alumina, zirconia or both. The support component preferably has a surface area of 50 to 700 square meters per gram, more preferably 400 to 600 square meters per gram, and preferably has a pore volume of 0.5 to 4 cubic centimeters per gram, more preferably 2 to 3 cubic centimeters per gram.

The chromium component can be combined with the support component using various methods, such as, for example, forming a co-precipitated tergel of silica, titanium, and chromium. Alternatively, an aqueous solution of a water soluble chromium component can be added to a hydrogel of the support component. Suitable water soluble chromium components include, but are not limited to, chromium nitrate, chromium acetate, and chromium trioxide. Alternatively, a solution of a hydrocarbon soluble chromium component such as tertiary butyl chromate, a diarene chromium compound, biscyclopentadienyl chromium (II), or chromium acetyl acetonate, can be used to impregnate a zerogel, which results from removal of water from a cogel. The chromium component is preferably used in an amount sufficient to give 5 weight percent (wt %) chromium or more, 10 weight percent chromium or more, 15 weight percent chromium or more, or 20 weight percent chromium or more, and 35 weight percent chromium or less, 30 weight percent chromium or less, 25 weight percent chromium or less, or 20 weight percent chromium or less, based on the total weight of the chromium component and the support component.

The catalyst is preferably arranged in a fixed bed configuration in the reactor. The catalyst may be used to perform the alkane dehydrogenation reaction for as long as the catalyst retains cost-effective catalytic activity.

The single-pass conversion of the alkane in the dehydrogenation reactor is preferably 35% or greater, more preferably 40% or greater, 45% or greater, 50% or greater, 55% or greater, 60% or greater, 65% or greater, 70% or greater, 75% or greater, 80% or greater, 85% or greater, 90% or greater, or 95% or greater. Unreacted alkane may be separated from the product stream leaving the dehydrogenation reactor, for example by an alkane-alkene splitter, and recycled to the feed entering the reactor. The overall conversion of the alkane is preferably 70% or greater, 75% or greater, 80% or greater, 85% or greater, 90% or greater, 95% or greater, 96% or greater, 97% or greater, 98% or greater, or 99% or greater. The selectivity of the alkane to the desired alkene (for example, the selectivity of isobutane to isobutene) is preferably 50% or greater, more preferably 55% or greater, 60% or greater, 65% or greater, 70% or greater, 75% or greater, 80% or greater, 85% or greater, 90% or greater, 95% or greater, 96% or greater, 97% or greater, 98% or greater, or 99% or greater.

During cyclic reactor operation, the amount of time spent per reduction cycle in one reactor configuration before switching configurations may vary depending on how quickly $CrO_3$ is converted to $Cr_2O_3$ in the catalyst performing the alkane dehydrogenation.

Set forth below are some embodiments of the processes disclosed herein.

Embodiment 1

A process of dehydrogenating an alkane to an alkene, comprising: (a) feeding CO to a reactor containing a catalyst comprising $CrO_3$; (b) contacting the CO with the $CrO_3$, to form $Cr_2O_3$ and $CO_2$; then (c) feeding an alkane to the reactor; and (d) contacting the alkane with the catalyst to form an alkene and $H_2$.

Embodiment 2

The process of Embodiment 1, wherein the catalyst further comprises an alumina or zirconia support.

Embodiment 3

A process of dehydrogenating an alkane to an alkene, comprising: (a) feeding CO to a first reactor containing a catalyst comprising $CrO_3$; (b) contacting the CO with the $CrO_3$, to form $Cr_2O_3$ and $CO_2$; (c) feeding the $CO_2$ obtained in (b), and an alkane, to a second reactor containing a catalyst comprising $Cr_2O_3$; (d) contacting the alkane with the catalyst in the second reactor to form an alkene and $H_2$; (e) reacting the $CO_2$ from (c) with the $H_2$ from (d), in the second reactor, to form CO and $H_2O$; and (f) feeding the CO formed in (e) to (a).

Embodiment 4

The process of Embodiment 3, further comprising performing (a)-(f) for a time X, and then performing (a')-(f') for a time X': (a') feeding CO to the second reactor containing a catalyst comprising $CrO_3$; (b') contacting the CO with the $CrO_3$, to form $Cr_2O_3$ and $CO_2$; (c') feeding the $CO_2$ obtained in (b'), and an alkane, to the first reactor containing a catalyst comprising $Cr_2O_3$; (d') contacting the alkane with the catalyst in the first reactor to form an alkene and $H_2$; (e') reacting the $CO_2$ from (c') with the $H_2$ from (d'), in the first reactor, to form CO and $H_2O$; and (f') feeding the CO formed in (e') to (a'); wherein (a)-(f) for the time X and (a')-(f') for the time X' are switched cyclically.

Embodiment 5

The process of any of Embodiments 3-4, wherein the catalyst comprising $CrO_3$ and the catalyst comprising $Cr_2O_3$ further comprise an alumina or zirconia support.

Embodiment 6

The process of any of Embodiments 1-5, wherein the alkane is a $C_2$-$C_{10}$ alkane.

Embodiment 7

The process of any of Embodiments 1-6, wherein the alkane is a $C_3$-$C_5$ alkane.

Embodiment 8

The process of any of Embodiments 1-7, wherein the alkane is isobutane.

Embodiment 9

The process of any of Embodiments 1-8, wherein the catalyst comprising $CrO_3$ comprises 10 wt % to 35 wt % chromium, based on the total weight of chromium component and support component.

Embodiment 10

The process of any of Embodiments 1-9, wherein the catalyst comprising $CrO_3$ comprises 15 wt % to 30 wt % chromium, based on the total weight of chromium component and support component.

Embodiment 11

The process of any of Embodiments 1-10, wherein a single-pass conversion of the alkane is 85% or greater.

Embodiment 12

The process of any of Embodiments 1-11, wherein the contacting of the CO with the $CrO_3$ is at a temperature of 550 to 600° C. and a pressure of 0.8 to 1.2 atm.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

What is claimed is:

1. A process of dehydrogenating an alkane to an alkene, comprising:
   (a) feeding CO to a first reactor containing a catalyst comprising $CrO_3$;
   (b) contacting the CO with the $CrO_3$, to form $Cr_2O_3$ and $CO_2$;
   (c) feeding the $CO_2$ obtained in (b), and an alkane, to a second reactor containing a catalyst comprising $Cr_2O_3$;
   (d) contacting the alkane with the catalyst comprising $Cr_2O_3$ in the second reactor to form an alkene and $H_2$;
   (e) reacting the $CO_2$ from (c) with the $H_2$ from (d), in the second reactor, to form CO and $H_2O$; and
   (f) feeding the CO formed in (e) to (a).

2. The process of claim 1, further comprising performing (a)-(f) for a time X, and then performing (a')-(f') for a time X'
   (a') feeding CO to the second reactor containing a catalyst comprising $CrO_3$;
   (b') contacting the CO with the $CrO_3$, to form the $Cr_2O_3$ and $CO_2$;
   (c') feeding the $CO_2$ obtained in (b'), and an alkane, to the first reactor containing a catalyst comprising $Cr_2O_3$;
   (d') contacting the alkane with the catalyst comprising $Cr_2O_3$ in the first reactor to form an alkene and $H_2$;
   (e') reacting the $CO_2$ from (c') with the $H_2$ from (d'), in the first reactor, to form CO and $H_2O$; and
   (f') feeding the CO formed in (e') to (a');
   wherein (a)-(f) for the time X and (a')-(f') for the time X' are switched cyclically.

3. The process of claim 1, wherein the catalyst comprising $CrO_3$ and the catalyst comprising $Cr_2O_3$ further comprise an alumina or zirconia support.

4. The process of claim 1, wherein the alkane is a $C_2$-$C_{10}$ alkane.

5. The process of claim 1, wherein the alkane is a $C_3$-$C_5$ alkane.

6. The process of claim 1, wherein the alkane is isobutane.

7. The process of claim 1, wherein the catalyst comprising $CrO_3$ further comprises a support component and comprises 10 wt % to 35 wt % chromium, based on a total weight of chromium and the support component.

8. The process of claim 7, wherein the catalyst comprising $CrO_3$ comprises 15 wt % to 30 wt % chromium, based on a total weight of chromium and the support component.

9. The process of claim 1, wherein a single-pass conversion of the alkane is 85% or greater.

10. The process of claim 1, wherein the contacting of the CO with the $CrO_3$ is at a temperature of 550 to 600° C. and a pressure of 0.8 to 1.2 atm.

11. A process of dehydrogenating an alkane to an alkene, comprising:
    (a) feeding CO to a reactor containing a catalyst comprising $CrO_3$ and a support component;
    (b) contacting the CO with the $CrO_3$ at a temperature of 550 to 600° C. and a pressure of 0.8 to 1.2 atm, to form $Cr_2O_3$ and $CO_2$; then
    (c) feeding a $C_3$-$C_5$ alkane to the reactor; and
    (d) contacting the alkane with the catalyst to form an alkene and $H_2$;
    wherein the catalyst comprising $CrO_3$ comprises 15 wt % to 35 wt % chromium, based on a total weight of chromium and the support component.

* * * * *